United States Patent [19]

Teass, Jr. et al.

[11] 4,329,650
[45] May 11, 1982

[54] ULTRA-CLEAN CELL ASSEMBLY

[75] Inventors: Horace A. Teass, Jr., Armonk, N.Y.; Patrick F. McKernan, Middletown, N.J.

[73] Assignee: McNab Incorporated, Mount Vernon, N.Y.

[21] Appl. No.: 119,042

[22] Filed: Feb. 5, 1980

[51] Int. Cl.³ ............................................. G01N 27/42
[52] U.S. Cl. ...................................... 324/450; 324/449
[58] Field of Search ........................ 324/438, 449, 450

[56] References Cited

U.S. PATENT DOCUMENTS 2,780,773  2/1957  Channon, Jr. ...................... 324/449

Primary Examiner—Michael J. Tokar
Attorney, Agent, or Firm—Peck & Peck

[57] ABSTRACT

A simplified clean conductivity or pH cell assembly comprising a solid plastic cell body and a test fluid conduit comprising a clean pipe fitting, affixed to the forward face of the solid body by means of an external clamp and a seal such as an O-ring. The clean pipe fitting is preferably formed of stainless steel and the internal surface thereof which comes in contact with the test fluid is plane and has no crevices or the like which could cause contamination of the fluid.

Pencil shaped electrodes are fixed in said solid body and extend therefrom into the test fluid in the conduit to be measured. The face of the solid body which is in contact with the test fluid is plane with no cavities, crevices, holes, projections, restricted channels, or the like. The electrodes for conductivity or pH measurement are cleanly formed of glass or stainless steel or other suitable material and have no surfaces which might result in contamination or the collection therein of dirt and the like. A temperature compensating network is in the solid body and an electrical connection from one electrode extends to this temperature compensating network, and an insulated feed-through is provided which contains electrical connections from the electrodes and the temperature compensating network and leads to a measuring or indicating instrument.

8 Claims, 2 Drawing Figures

U.S. Patent May 11, 1982 4,329,650
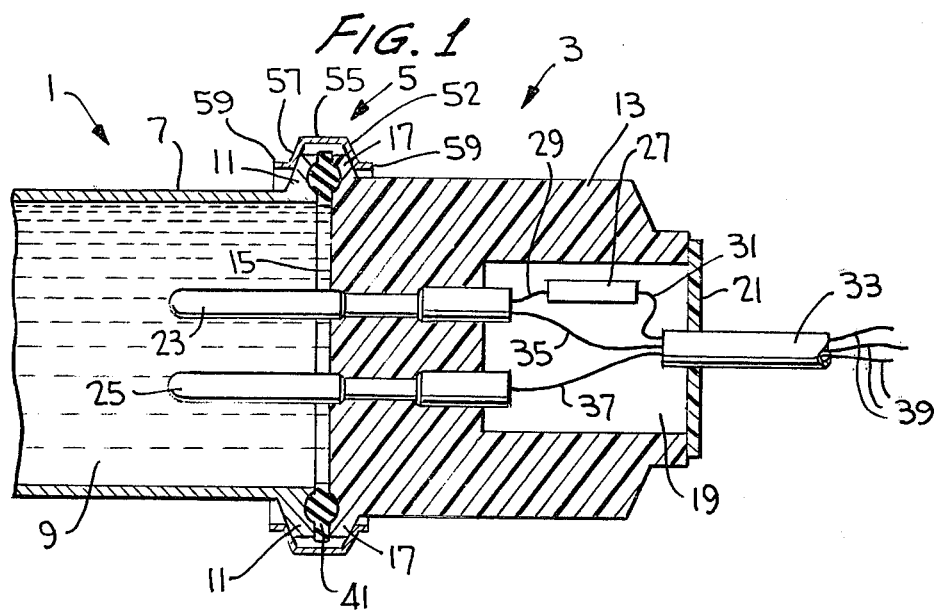
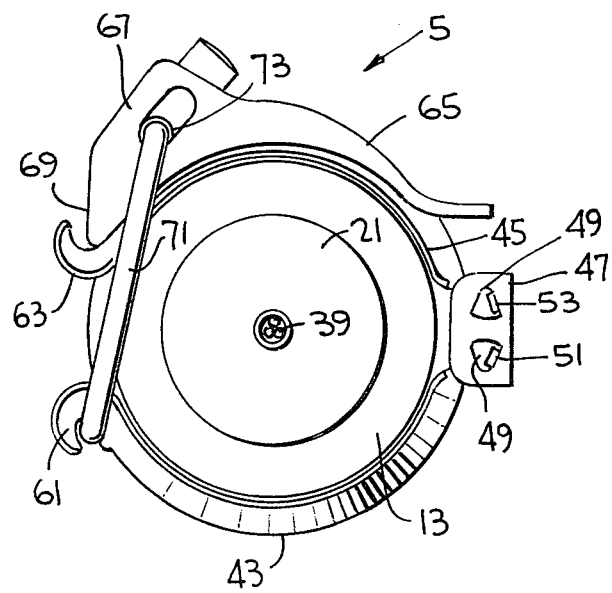

ULTRA-CLEAN CELL ASSEMBLY

BRIEF SUMMARY OF THE INVENTION

An ultra-clean cell assembly for the measurement of electrical conductivity or pH in applications where purity, cleanliness, lack of contamination, prevention of water entrapment are of utmost importance. The assembly comprises an interchangeable clean cell, easily and rapidly disassembled and cleaned, attached to standard clean system piping via an O-ring (or gasket) and an external clamp. All parts exposed to the process or test fluid contain no internal threads, crevices, holes, restricted channels, projections or other sites for dirt retention, cross contamination, or standing water entrapment.

BRIEF DESCRIPTION OF THE SEVERAL VIEWS OF THE DRAWING

FIG. 1 is a sectional view of the conductivity cell with the electrodes extending into the test fluid within the pipe fitting.

FIG. 2 is a rear end view of the conductivity cell illustrating the external clamping mechanism for securely attaching the pipe fitting to the cell body in a leak-proof manner.

DETAILED DESCRIPTION

There has been a long felt need by manufacturers and users of pharmaceuticals, fine chemicals and preparations for internal bodily use for a simple ultra-clean, reliable, easily interchangeable device which is readily cleaned so that various conductivity or pH sensors may be inserted into a piping system without causing contamination, long interruption, or other problems which are now encountered in devices in this art.

This invention has overcome the problems presented above, as well as other problems which are now met in this field, and it has eliminated the necessity that each specific sensor or electrode has to be externally preassembled into its own container and carefully examined for cleanliness and sites for possible contamination, and then be slowly inserted into a disassembled or shutdown operation. Also, in the prior art several measuring set-ups could be connected at one time, with suitable valving; however, it has been our experience that such arrangements lead to the distinct possibility of cross-contamination. It has been our further experience that such assemblies have often led to problems with crevices, holes, internal threads, restricted channels, projects and the like which serve as collection and retention points for unwanted materials.

All of the above mentioned drawbacks, and others, which are inherent in prior art devices have been overcome by this invention.

The assembly and arrangement of this invention has been designed for the determination of electrical conductivity and/or pH in the manufacture and use of pharmaceuticals, fine chemicals, solutions for internal use, and the like, and where absolute purity and prevention of any possible contamination is a primary prerequisite.

In the accompanying drawing the numeral 1 has been used to designate in its entirety a clean piping fitting while the numeral 3 has been used to designate in its entirety the body of the conductivity cell and the numeral 5 has been used to designate in its entirety the mechanism by means of which the piping fitting 1 is affixed and sealed to the cell body 3. A piping fitting 7 is utilized and may comprise a stainless steel clean piping fitting base and contains the body of the processor test fluid 9 the conductivity or pH measurement of which is to be taken. The clean piping fitting 7 at one end thereof is provided with a radially outwardly extending flange 11, the purpose of which will be fully explained as this description proceeds.

The conductivity cell 3 comprises a body 13 which, as will be explained, is adapted to be sealed to the piping fitting 7, the body 13 is formed of a clean plastic and what we shall term the "operative face" 15 thereof is a smooth plane surface having no crevices, holes or the like therein to fully and entirely avoid contamination of the test fluid 9. At its operative end the body 13 is provided with a radially outwardly extending flange 17, for a purpose to be hereinafter described. The body 13 is formed to provide a hollow or free area 19 therein which is closed at its rear end by an exterior cap 21. Projecting forwardly from the cell body 13 are a pair of pencil shape electrodes 23 and 25 which extend forwardly from the cell body and into the test fluid 9 and these electrodes 23 and 25 function to measure the conductivity, or pH of the test fluid 9. The electrodes 23 and 25 are formed in any suitable manner within the plastic body 13 to extend therefrom and therethrough and to open at their rear ends into the hollow or free area 19 in the cell body 13. A temperature compensating network 27 is mounted in any suitable manner in the open area and the electrode 23 is electrically connected to the temperature compensating network 27 by conductor 29, the temperature compensating network being connected as at 31 to an insulated feed-through 33. The electrode 23 is connected by a conductor 35 to the feed-through 33 as is the electrode 25 by a conductor 37. Thus, the feed-through 33 contains the electrical connections from the electrodes and the temperature conpensating network and leads as at 39 to a measuring indicating instrument which is not shown since it does not involve any of the inventive subject matter of this invention. The sensors or electrodes 23 and 25 may be formed of any suitable plastic, metal and/or glass.

The cell 3 is assembled to the clean pipe fitting 7 and sealed and clamped thereto in a leak-proof manner by means of O-ring 41 or other suitable sealing means, which is disposed between the flange 11 of the pipe fitting 7 and the flange 17 of the conductivity cell, the flanges 11 and 17 having semicircular recesses therein to receive the O-ring 41, all as is particularly illustrated in FIG. 1 of the drawings. With the cell 3 and the pipe fitting 7 of the O-ring 41 positioned therebetween the conductivity cell and the pipe fitting 7 are releasably locked or clamped together in leak-proof position by means of an external clamping mechanism.

The clamping mechanism 5 includes a pair of arcuate shaped members 43 and 45 which partially encircle the conductivity cell and pipe fitting 7 and at their rear ends are secured to an anchor plate 47 having apertures 49 therein which moveably receive the ends 51 and 53 of the members 43 and 45. Each member 43 and 45 is shaped to provide an outer flat top portion 55 from each side of which downwardly and outwardly depends a leg 57 which preferably terminates in a pair of feet 59. The downwardly and outwardly depending legs 57 bear against the flanges 11 and 17, respectively, to soundly and securely affix together the conductivity cell 3 and the pipe fitting 1. Each arcuate member 43 and 45 is provided with a hook nose 61 and 63, respectively. The clamping mechanism 5 includes mechanism for releasably clamping the members 43 and 45 in operative clamping and sealing position as especially illustrated in FIG. 1 of the drawings. This mechanism comprises an operating lever 65 for manual operation to releasably produce the aforesaid clamping action of the members 43 and 45. The lever 65 terminates in a block-like element 67 having a nose 69 which operatively extends into the nose 63 of the member 45. A link element 71 extends through a slot 73 which is provided in the block-like portion 67 and then such link extends into and about the hook nose 61 of the member 43. It will now be recognized that when the clamping mechanism 5 is in the position illustrated in FIG. 2 of the drawings it functions to urge the members 43 and 45 together to clamp the conductivity cell and the pipe 1 together with the 0-ring disposed between the flanges 11 and 17 to provide leak-proof affixation of the pipe fitting and the cell together. When the lever 65 is moved upwardly the clamping action by the nose 69 and the link 71 will be released so that the cell may be removed from the pipe fitting. It is significant that this clamping mechanism is externally mounted relative to the pipe fitting in the cell so that it in no way comes into contact with the test fluid to thereby possibly cause contamination, nor are any threads or like arrangements used which might cause contamination. The particularly disclosed clamping mechanism is shown merely by way of example and is not to be considered as a limitation, for any suitable type of external clamping means may be used and still fall within the spirit and scope of this invention.

What is claimed is:

1. A conductivity cell assembly including, a combination, a piping fitting and a conductivity cell having a pair of electrodes, said piping fitting having an open end and said cell being in juxtaposition to said end and having an end disposed in operative position in engagement with the periphery of said open end of said piping fitting which houses a fluid to be tested and said electrodes projecting from said end of the cell into the fluid with said end of said conductivity cell being in contact with the test fluid, and external fastening means extending externally about said conductivity cell and said piping fitting and operable externally thereof for releasably maintaining said cell and said piping fitting together at their juxtaposed ends.

2. A conductivity cell assembly in accordance with claim 1, wherein said fastening means comprises a clamping mechanism externally engaging the juxtaposed ends of the piping fitting and the cell of the conductivity cell assembly.

3. A conductivity cell assembly in accordance with claim 1, wherein said conductivity cell includes a solid body and said end thereof is plane and smooth and is in contact with the test fluid within the piping fitting with the internal circumferential surface of said piping fitting being plane and smooth.

4. A conductivity cell assembly in accordance with claim 3, wherein the perimeter of said open end of said piping fitting is provided with a circumferential radially outwardly extending flange, and the solid body of the conductivity cell is provided with a circumferentially radially outwardly extending flange which extends from the plane, smooth end of the solid body, said clamping mechanism operatively engaging said two flanges so as to urge the ends of the cell and the piping fitting together and maintain the conductivity cell and the piping fitting in operative leak-proof end to end position.

5. A conductivity cell assembly in accordance with claim 4, wherein a compressible sealing means is disposed between said two flanges.

6. A conductivity cell assembly in accordance with claim 5, wherein each of said flanges has a downwardly extending inclined surface on the outer sides thereof and said clamping mechanism is provided with downwardly extending inclined means in contact with the inclined surfaces of said two flanges and when said clamping mechanism is in operative clamping position said means urge said flanges toward one another to compress said sealing means therebetween providing a leak-proof seal.

7. A conductivity cell assembly in accordance with claim 3, wherein said solid body is formed of plastic and is provided with an open area therein and said electrodes extend from the test fluid and through said body and into said open area.

8. A conductivity cell assembly in accordance with claim 7, wherein electrical leads extend from said electrodes and into the open area and one of said leads is connected to a temperature compensating network which is disposed in the open area.

* * * * *